United States Patent [19]
Ardelt

[11] Patent Number: 5,559,212
[45] Date of Patent: Sep. 24, 1996

[54] FROG EMBRYO AND EGG-DERIVED TUMOR CELL ANTI-PROLIFERATION PROTEIN

[75] Inventor: Wojciech J. Ardelt, Passaic, N.J.

[73] Assignee: Alfacell Corporation, Bloomfield, N.J.

[21] Appl. No.: 283,970

[22] Filed: Aug. 1, 1994

Related U.S. Application Data

[63] Continuation of Ser. No. 814,332, Feb. 3, 1992, which is a continuation-in-part of Ser. No. 436,141, Nov. 13, 1989, abandoned, which is a continuation-in-part of Ser. No. 178,118, Apr. 6, 1988, Pat. No. 4,882,421.

[51] Int. Cl.⁶ .................................................. C07K 14/475
[52] U.S. Cl. ...................................................... 530/350
[58] Field of Search .................................. 530/350, 395; 424/946; 435/199; 514/12, 21

[56] References Cited

U.S. PATENT DOCUMENTS

| | | | |
|---|---|---|---|
| 4,289,690 | 9/1981 | Pertha et al. | 530/351 |
| 4,882,421 | 11/1989 | Shogen et al. | 530/350 |

OTHER PUBLICATIONS

Shibaya et al. 1989, Biosis Number: 89101888 of Development 106(4): 799–808.
Shibiya et al. 1988. File 155 Accession No. 88313378 of Dev Biol. 129(1): 253–264.
Sigma Chemical Co. Price List, 1988, St. Louis, No. p. 1023.
Hird et al. 1990. Genes and Cancer, Corney et al (eds.), John Wiley & Sons Ltd., NY, pp. 183–189.
Ardelt et al. 1991. J. Biol Chem. 266(1): 245–251.

*Primary Examiner*—Robert A. Wax
*Assistant Examiner*—K. Cochrane Carlson

[57] ABSTRACT

*Rana pipiens* eggs are subjected to fertilization and the embryos are grown to a predetermined stage of development. The embryos and unfertilized eggs are then subjected to mechanical processing in the presence of a weakly acidic buffer to produce an extract. The extract is subjected to ion-exchange chromatography and size-exclusion chromatography.

The resulting pharmaceutical has activity against certain cancer cells. The amino acid sequence and composition of the pharmaceutical are disclosed.

1 Claim, 2 Drawing Sheets

```
           1   2   3   4   5   6   7   8   9   10
        <Glu-Asp-Trp-Leu-Thr-Phe-Gln-Lys-Lys-His- 11                                  20
         Ile-Thr-Asn-Thr-Arg-Asp-Val-Asp-Cys-Asp- 21                                  30
         Asn-Ile-Met-Ser-Thr-Asn-Leu-Phe-His-Cys- 31                                  40
         Lys-Asp-Lys-Asn-Thr-Phe-Ile-Tyr-Ser-Arg- 41                                  50
         Pro-Glu-Pro-Val-Lys-Ala-Ile-Cys-Lys-Gly- 51                                  60
         Ile-Ile-Ala-Ser-Lys-Asn-Val-Leu-Thr-Thr- 61                                  70
         Ser-Glu-Phe-Tyr-Leu-Ser-Asp-Cys-Asn-Val- 71                                  80
         Thr-Ser-Arg-Pro-Cys-Lys-Tyr-Lys-Leu-Lys- 81                                  90
         Lys-Ser-Thr-Asn-Lys-Phe-Cys-Val-Thr-Cys- 91                                 100
         Glu-Asn-Gln-Ala-Pro-Val-His-Phe-Val-Gly- 101         104
         Val-Gly-Ser-Cys
```

FIG. 2

```
  1   2   3   4   5   6   7   8   9  10
<Glu-Asp-Trp-Leu-Thr-Phe-Gln-Lys-Lys-His- 11                                    20
Ile-Thr-Asn-Thr-Arg-Asp-Val-Asp-Cys-Asp- 21                                    30
Asn-Ile-Met-Ser-Thr-Asn-Leu-Phe-His-Cys- 31                                    40
Lys-Asp-Lys-Asn-Thr-Phe-Ile-Tyr-Ser-Arg- 41                                    50
Pro-Glu-Pro-Val-Lys-Ala-Ile-Cys-Lys-Gly- 51                                    60
Ile-Ile-Ala-Ser-Lys-Asn-Val-Leu-Thr-Thr- 61                                    70
Ser-Glu-Phe-Tyr-Leu-Ser-Asp-Cys-Asn-Val- 71                                    80
Thr-Ser-Arg-Pro-Cys-Lys-Tyr-Lys-Leu-Lys- 81                                    90
Lys-Ser-Thr-Asn-Lys-Phe-Cys-Val-Thr-Cys- 91                                   100
Glu-Asn-Gln-Ala-Pro-Val-His-Phe-Val-Gly- 101       104
Val-Gly-Ser-Cys
```

5,559,212

1

FROG EMBRYO AND EGG-DERIVED TUMOR CELL ANTI-PROLIFERATION PROTEIN

This application is a continuation of Ser. No. 07/814,332, filed Feb. 3, 1992, now abandoned, which is a continuation-in-part of Ser. No. 07/436,141, filed Nov. 13, 1989, now abandoned, which is a continuation-in-part of Ser. No. 07/178,118, filed Apr. 6, 1988, now U.S. Pat. No. 4,882,421.

BACKGROUND OF THE INVENTION

The invention relates to pharmaceuticals, and more particularly relates to pharmaceuticals for use in treating tumors in humans.

At present, tumors are treated either by chemotherapy, radiotherapy or surgery. Each of these therapies has disadvantages.

It would be advantageous to avoid the disadvantages of chemotherapy, radiotherapy and surgery.

One object of the invention is to provide a pharmaceutical therapy for tumors in humans.

Another object is to provide such a therapy which has less disadvantageous side effects than those of other known therapies.

A further object is to provide such a therapy for use with more than one type of tumor.

Still a further object is, in general, to improve on known therapies for treatment of tumors in humans.

In accordance with the invention, there is provided a pharmaceutical for treatment of tumors in humans. The pharmaceutical is a pure protein having a molecular weight of approximately 12,000 Daltons by mass spectrometry (approximately 14,500 Daltons by electrophoresis), a characteristic isoelectric point by isoelectric focussing and a characteristic amino acid composition. Advantageously although not necessarily, the pharmaceutical is derived from frog eggs subjected to fertilization; in a preferred embodiment, the pharmaceutical is derived from embryos and eggs of the *Rana pipiens* frog. The development of the embryos is advantageously halted before gastrulation and preferably at or before the full blastulae (128 cell) stage, and the embryos are homogenized in the presence of a weakly acidic buffer and then centrifuged to derive a supernatant liquid. This is then subjected to ion-exchange chromatography and size-exclusion chromatography.

BRIEF DESCRIPTION OF THE DRAWINGS

The invention will be better understood with reference to the following illustrative and non-limiting drawings, in which:

FIG. 2 is an illustration of the sequence of amino acids in the pharmaceutical.

DETAILED DESCRIPTION OF PREFERRED EMBODIMENTS

A. Production of Embryo/Egg Mixture

Figure 1:
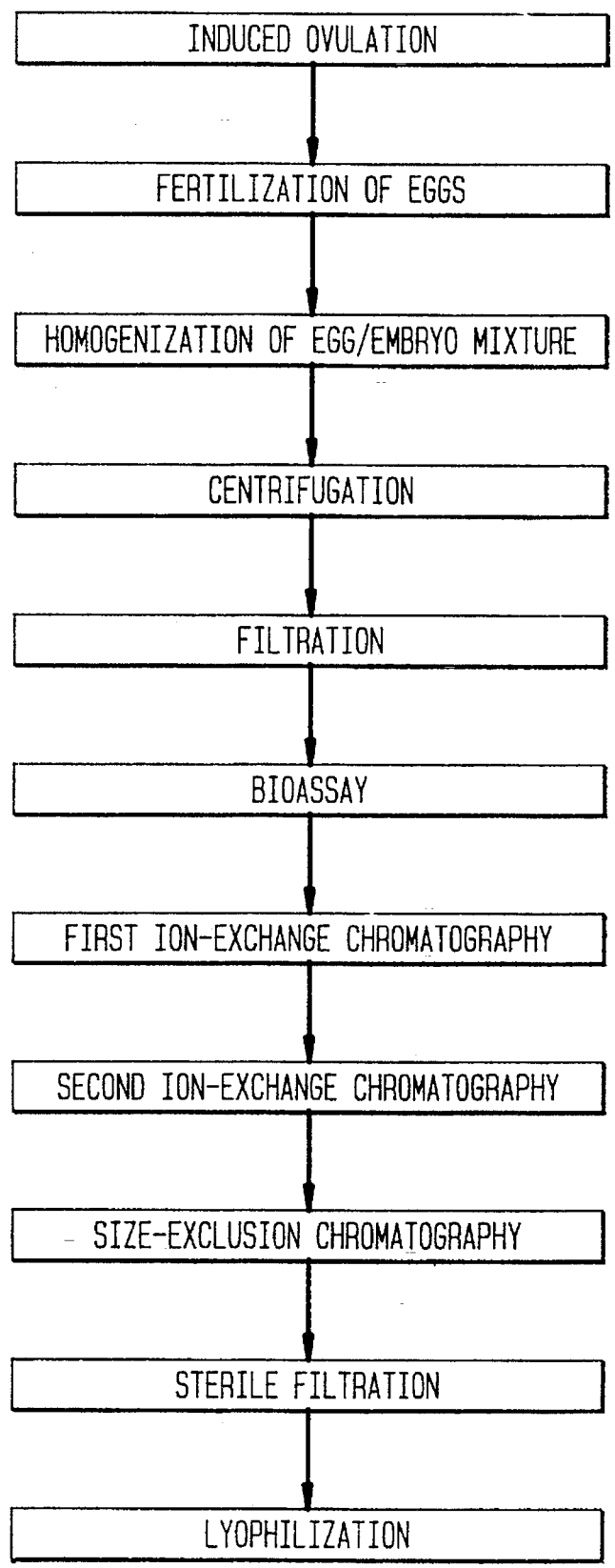
FIG. 1 is a flow chart of the process in accordance with a preferred embodiment of the invention.

In the preferred embodiment, *Rana pipiens* eggs are produced by induced ovulation (so that their development takes place in a highly controlled manner) and fertilized under controlled conditions outside the body of the female frog. Ovulation is only induced during the months from September through March; during the other months, induced ovulation is not feasible. This is because *Rana pipiens* ovulates spontaneously in the month of April and its breeding season lasts from May through August.

Only large, healthy and vigorous gravid female *Rana pipiens* are selected for induced ovulation. They are separated from male *Rana pipiens* and are maintained at a temperature of 6° C. for a period of three days in tanks filled with one inch of tap water. This temperature is preferred, but other temperatures can be used if the other variables in the fertilization process are accordingly adjusted; the rate at which the eggs develop is dependent upon temperature.

For each selected female, a petri dish is preferably filled with 10 cubic centimeters of tested spring water. Tested spring water is fresh spring water which has been tested to support life of *Rana pipiens* and its embryos.

Advantageously, each selected female is induced to ovulate by introducing 5 freshly isolated female *Rana pipiens* pituitary glands into her body. Male pituitary glands may be substituted for female pituitary glands, but one female pituitary gland is equivalent to two male pituitary glands and the quantities used must be adjusted accordingly.

The appropriate number of glands is placed in the corresponding liquid-containing petri dish. Each selected female is brought to room temperature (22° C.). Dish by dish, the glands are drawn up into a syringe and introduced into the right lower quadrant of the abdomen of the corresponding selected female by injection through an 18 gauge needle.

The selected females are then replaced in tanks filled with one inch of spring water. Flat rocks are placed in the bottom of each tank, so that the females can rest upon them and remain above the water line. (This is advantageous because gravid females can become lethargic and may drown if not held above the water line.) The tanks are covered with warehouse cloth (to prevent the frogs from jumping out of the tanks) and advantageously kept at room temperature (22° C.) for 48 hours. The eggs produced by the gravid females are then, in accordance with the preferred embodiment, subjected to fertilization outside the bodies of the female frogs, advantageously in petri dishes, and preferably in 4 petri dishes per gravid female.

To accomplish this fertilization, male *Rana pipiens* are sacrificed (as by over-etherization) and their testes are removed and cleaned of connective tissue and fat. Enough males must be killed to yield at least 4 testes per petri dish of eggs to be fertilized (i.e. 16 testes per gravid female). This quantity produces an optimized quantity of sperm suspension considering the size of the petri dishes. (Advantageously, the pituitary glands of the male *Rana pipiens* are also removed for subsequently inducing ovulation in other females.)

Four testes are then placed in each petri dish, and the testes are macerated (as by chopping) to form a milky sperm suspension. The maceration must be conducted in such a manner as not to chop the sperm. The eggs are then removed from each gravid female by pressing her abdomen towards her posterior. The egg production of each female is distributed evenly among four suspension-filled petri dishes; this avoids overcrowding the eggs in the dishes.

The eggs are left in the suspension for about 3 to 4.5 hours at room temperature. During the first hour, the sperm suspension and eggs in the dish are intermittently swirled so that the eggs are always covered by the sperm suspension. After the 3 to 4.5 hours have passed, the dishes are checked under a dissecting microscope for signs of cleavage. When 80% cleavage of the *Rana pipiens* embryos is observed, the corresponding dish is collected; the embryos are then in at least the 4 cell stage of development. The 4 cell stage of development is used as a benchmark because it establishes division of the eggs and the existing fact of fertilization cannot be overlooked.

Since 100% cleavage of the embryos is not ordinarily achieved in the stated 3 to 4.5 hour time, the collected dishes will ordinarily contain both embryos (fertilized eggs) and unfertilized eggs. This mixture will be occasionally referred to as a mixture of eggs subjected to fertilization, meaning that both eggs and embryos are present. Since 80% cleavage is used as a benchmark in the preferred embodiment, the ratio of eggs to embryos in the mixture is approximately 1:4.

All collected eggs subjected to fertilization may then be scraped into containers and stored in frozen form at −15° C. to −20° C. This storage is not essential for the practice of the invention; it is preferred only when it is convenient to carry out subsequent processing in batches.

B. Mechanical Processing of the Eggs Subjected to Fertilization

If the mixture has been frozen, it is thawed by any method which does not overheat it. The thawed or never-frozen mixture is then homogenized in the presence of a weakly acidic buffer, preferably under a laminar air flow hood to avoid contamination.

In the preferred embodiment, the mixture of eggs subjected to fertilization is mixed, at room temperature, with 0.15M sodium acetate (pH 4.8–4.9) using two volumes of buffer for one like volume of the mixture of eggs subjected to fertilization. The buffer need not be sodium acetate but must be weakly acidic; sodium acetate is used because, in the preferred embodiment, S-Sepharose chromatography is carried out and sodium acetate is a good buffer within a pH range of 4–5.8 (in which range S-Sepharose exchange columns are efficient). Homogenization is carried out in a Waring Blender until all eggs have been disrupted as observed visually, but a Waring Blender is not required and any sanitary method for accomplishing thorough homogenization can be used. Homogenization is complete when the suspension appears homogenous with no visual sign of intact eggs. The homogenate is then stirred at room temperature for 2 hours, and kept frozen until further processing is to be carried out.

In the preferred embodiment, the stirred homogenized mixture of eggs subjected to fertilization (which mixture was kept frozen for at least a week and then thawed) is centrifuged (at 4° C. to 8° C.) in two stages. In the first stage, the stirred homogenate is centrifuged at an average acceleration of 34,000× g and the resulting supernatant is saved. The time required for this step is usually 60 minutes, but it is necessary to obtain clear and gel-free supernatant and the time is increased as necessary to achieve this. In the second stage, the sediment pellet which results from the first stage of centrifugation is re-homogenized as above. The re-homogenized sediment is then centrifuged as above, and the resulting supernatant is then pooled with the supernatant produced in the first step.

The duration, speed, and other particulars of the centrifugation steps described above are not required to practice the invention, but they are optimized for the preferred embodiment of the invention.

As each batch of supernatant fluid is decanted, it is filtered through a layer of DEAE-Sepharose equilibrated in the extraction buffer (0.15M sodium acetate, pH 4.8–4.9). This is to remove debris which could clog the columns in the processing steps described below, but the use of DEAE-Sepharose is not required and other suitable filters could be used instead.

In the preferred embodiment, the filtered extract is assayed for bioactivity against a predetermined cell line. This is not required but, for two main reasons, is advantageous. The first reason is that in a process which is scaled to commercial production quantities, batches of filtered extract are pooled together before subsequent processing steps are undertaken. By checking for and discarding batches of inactive filtered extract, inadvertent contamination of bioactive batches with nonbioactive ones is eliminated. The other reason is that the subsequent processing steps are expensive, and identification and rejection of nonbioactive material saves the substantial expense which would otherwise be wasted on processing it. However, even though an assay is presently preferred, no assayed batch of filtered extract has ever been found to be inactive and the use of an assay must therefore be considered entirely optional.

The actual assay used in the preferred embodiment is performed using human submaxillary epidermoid carcinoma A-253 cells and a tetrazolium compound sold by Chemicon International, Inc., 100 Lomita Street, El Segundo, Calif., under the MTT trademark. However, this is not necessary and other bioassays may be used. Alternatively, a bioassay may be unnecessary if an alternate non-bioassay method which correlates well with a bioassay is available.

The filtered extract is advantageously immediately subjected to further purification steps.

C. Ion-Exchange Chromatography

The filtered extract is subjected to ion-exchange chromatography. In the preferred embodiment, the ion-exchange chromatography is carried out in two steps under slightly different conditions. During the first step, the active protein is initially isolated and essentially freed of endotoxin. During the second step, the protein is purified from other proteins which have been co-purified with the active protein during the first step as well as from any possible persisting endotoxin.

In the preferred embodiment, the first ion-exchange chromatography step is carried out using a column which is 11 cm in diameter and 20 cm long. The conditions described below are optimized for columns of these dimensions. However, if differently-dimensioned columns are used, the conditions may change.

In the preferred embodiment, the purpose of the two consecutive ion-exchange chromatography steps is to isolate proteins with isoelectric points pI of 9.5–10.5 (as determined by isoelectric focussing) before isolating the proteins by size. In the first ion-exchange chromatography step, the pH of the filtered extract is adjusted to 5.2 with ammonium hydroxide and loaded onto a column which is filled with S-Sepharose. The column is equilibrated in a 0.15M sodium acetate buffer (pH 5.2) and the column is developed with a continuous linear gradient of sodium chloride (0–0.5M) made in the equilibrating buffer. These conditions are not necessary to practice the invention but they are convenient and, at present, seem to produce good working yields of bioactive protein.

In the preferred embodiment, the eluted protein is then diluted 2 times with pyrogen-free water and subjected to a second ion-exchange chromatography step which is carried out under different conditions. This second ion-exchange chromatography step is performed on a second column which is 11 cm in diameter and 15 cm long and is filled with S-Sepharose. The column is equilibrated in a 0.15M sodium acetate buffer (pH 5.2) and the column is developed with a continuous linear gradient of sodium chloride (0–0.3M) made in the equilibrating buffer.

Advantageously, both chromatography steps are carried out at 18° C.–20° C. (air conditioned room), but this is not critical. Column chromatography is known to be more efficient above 4° C. (cold-room) temperatures and the process is carried out at the highest temperature which is consistent with stability of the purified pharmaceutical.

In the preferred embodiment, the eluate from the second ion-exchange step is alkalized to pH 6–7 with ammonium hydroxide, concentrated by ultrafiltration using a membrane which has a 5000 Daltons molecular weight cutoff and discarding the permeate. Suitable membranes are the Spectra-Por (manufactured by Spectrum Medical Industries) and the Amicon YM5 (manufactured by Amicon), but other membranes and other concentration procedures may be used instead.

D. Size-Exclusion Chromatography

The concentrated material is then loaded onto a column which is 11 cm in diameter and 50 cm long, which is filled with Bio-Gel P-30 gel and which is equilibrated in 0,075 ammonium bicarbonate. The main protein peak is isolated.

These specific conditions are not required to practice the invention; other dimensions, gels and even other size-exclusion techniques could be used instead. However, it is recommended that the size-exclusion chromatography follow the ion-exchange chromatography. This is because this order of chromatography makes it possible to use a column of reasonable size for the size-exclusion chromatography.

E. Final Processing

The eluate from the size-exclusion column is then sterile filtered through a 0.22 micron filter and subsequently lyophilized (freeze-dried). These process steps are standard in the pharmaceutical industry, and are not a part of the invention. The resultant preparation is devoid of viable micro-organisms.

Bioactivity of the Pharmaceutical

Confirmatory in vitro and in vivo animal data show that the pharmaceutical is active against human submaxillary epidermoid carcinoma A-253 cells and human ovarian adenocarcinoma NIH-OVCAR-3 cells. The pharmaceutical has also shown activity against human leukemic HL-60 cells, human COLO 320 DM cells originally isolated from colon adenocarcinoma, human LOX melanoma, and human lung squamous carcinoma HT-520 cells.

Chemical Analysis and Composition of the Pharmaceutical

The pharmaceutical described above has been well characterized chemically. While the pharmaceutical is a protein isolated from *Rana pipiens*, it is believed that the pharmaceutical may be produced using genetic engineering techniques, as long as the end result has the following chemistry and structure of the sequence depicted in FIG. 2.

The pharmaceutical is a pure protein (i.e. homogeneous, as established by standard tests which are used to assay the homogeneity of proteins). By electrophoresis, the molecular weight of the pharmaceutical is approximately 14,500 Daltons. Calculation of the molecular weight based upon the below listed amino acid sequence indicates that the molecular weight should be 11,860 Daltons. However, because metal ions may have bonded to the protein despite all efforts to remove them, and because different isotopes may be involved, the molecular weight of the pharmaceutical as determined by mass spectroscopy is 12,430 Daltons. In view of this discrepancy, the molecular weight of the pharmaceutical as determined by mass spectrometry will be considered to be approximately 12,000 Daltons. The pharmaceutical has an isoelectric point pI between 9.5 and 10.5, as determined by isoelectric focussing. The pharmaceutical has a blocked amino terminal group and is essentially free of carbohydrates (as determined by anthrone and orcinol methods).

The pharmaceutical has the following amino acid composition:

| Amino Acid Analysis | |
|---|---|
| AMINO ACID RESIDUE | MOL % (24 HOUR ACID HYDROLYSIS) |
| Aspartic acid/Asparagine | 13.99 |
| Threonine | 9.30 (Note 1) |
| Serine | 7.78 |
| Glutamic acid/Glutamine | 6.10 |
| Proline | 4.36 |
| Glycine | 3.09 |
| Alanine | 3.09 |
| Cystine/2 | 6.92 (Note 1) |
| Valine | 8.20 |
| Methionine | 0.85 (Note 1) |
| Isoleucine | 4.86 (Note 2) |
| Leucine | 5.22 |
| Tyrosine | 2.96 |
| Phenylalanine | 6.05 |
| Histidine | 2.88 |
| Lysine | 11.62 |
| Arginine | 2.70 |
| Tryptophan | Not Determined (Note 3) |
| Approximate Total | 99.97% |

Note 1: Threonine, cystine/2 and methionine are partially destroyed during hydrolysis and this value is uncorrected for such partial destruction.
Note 2: This value is uncorrected for incomplete hydrolysis.
Note 3: Tryptophan cannot be detected in acid hydrolysis of proteins because it is destroyed and is consequently shown as Not Determined. However, analysis of the ultraviolet spectrum revealed the presence of one tryptophan residue per molecule.

| Amino Acid Composition (as calculated from amino acid sequence) | |
|---|---|
| AMINO ACID | APPROX. # OF RESIDUES PER MOLECULE OF MATERIAL |
| Aspartic acid | 6 |
| Asparagine | 8 |
| Threonine | 10 |
| Serine | 8 |
| Glutamic acid | 3 |
| Pyroglutamic acid | 1 |
| Glutamine | 2 |
| Proline | 4 |
| Glycine | 3 |
| Alanine | 3 |
| Cystine/2 | 8 |
| Valine | 8 |
| Methionine | 1 |
| Isoleucine | 6 |
| Leucine | 5 |
| Tyrosine | 3 |
| Phenylalanine | 6 |
| Histidine | 3 |
| Lysine | 12 |
| Arginine | 3 |
| Tryptophan | 1 |
| Approximate Total | 104 |

The pharmaceutical has been sequenced. As is shown below, the total length of the sequence is believed to be 104 residues. The N-terminus of the protein is pyroglutamic acid (<Glu). This is a cyclized derivative of glutamic acid which is devoid of the free amino group necessary for direct sequencing and which therefore "blocks" the N-terminus of the protein.

When the shorter fragment described in the referenced parent application (application Ser. No. 07/178,118, filed Apr. 6, 1989) was cleaved with pyroglutamate aminopeptidase, pyroglutamic acid was removed from the shorter fragment, permitting sequencing to commence at the second residue. Such cleavage is a strong indication that the N-terminus is pyroglutamic acid since pyroglutamate aminopeptidase only cleaves pyroglutamic acid. The presence of pyroglutamic acid was further confirmed by mass spectrometry of the referenced shorter fragment. The molecular weight of this shorter fragment determined by mass spectrometry agreed well with the weight as calculated assuming that pyroglutamic acid was present and disagreed with the weight as calculated assuming that glutamic acid was present.

The pharmaceutical has the following amino acid sequence:

```
1    2    3    4    5    6    7    8    9    10
<Glu—Asp—Trp—Leu—Thr—Phe—Gln—Lys—Lys—His—

11                                            20
Ile—Thr—Asn—Thr—Arg—Asp—Val—Asp—Cys—Asp—

21                                            30
Asn—Ile—Met—Ser—Thr—Asn—Leu—Phe—His—Cys—

31                                            40
Lys—Asp—Lys—Asn—Thr—Phe—Ile—Tyr—Ser—Arg—

41                                            50
Pro—Glu—Pro—Val—Lys—Ala—Ile—Cys—Lys—Gly—

51                                            60
Ile—Ile—Ala—Ser—Lys—Asn—Val—Leu—Thr—Thr—

61                                            70
Ser—Glu—Phe—Tyr—Leu—Ser—Asp—Cys—Asn—Val—

71                                            80
Thr—Ser—Arg—Pro—Cys—Lys—Tyr—Lys—Leu—Lys—

81                                            90
Lys—Ser—Thr—Asn—Lys—Phe—Cys—Val—Thr—Cys—

91                                            100
Glu—Asn—Gln—Ala—Pro—Val—His—Phe—Val—Gly—

101       104
Val—Gly—Ser—Cys
```

It is possible, although not highly likely, that a few residues exist after the apparent C-terminus at position 104. This is because it has as yet been impossible to verify by chemical means that the C-terminus is cystine.

Although a preferred embodiment has been described above, the scope of the invention is limited only by the following claims:

I claim:

1. A homogeneous protein having the following amino acid sequence:

```
1    2    3    4    5    6    7    8    9    10
<Glu—Asp—Trp—Leu—Thr—Phe—Gln—Lys—Lys—His—

11                                            20
Ile—Thr—Asn—Thr—Arg—Asp—Val—Asp—Cys—Asp—

21                                            30
Asn—Ile—Met—Ser—Thr—Asn—Leu—Phe—His—Cys—

31                                            40
Lys—Asp—Lys—Asn—Thr—Phe—Ile—Tyr—Ser—Arg—

41                                            50
Pro—Glu—Pro—Val—Lys—Ala—Ile—Cys—Lys—Gly—

51                                            60
Ile—Ile—Ala—Ser—Lys—Asn—Val—Leu—Thr—Thr—

61                                            70
Ser—Glu—Phe—Tyr—Leu—Ser—Asp—Cys—Asn—Val—

71                                            80
Thr—Ser—Arg—Pro—Cys—Lys—Tyr—Lys—Leu—Lys—

81                                            90
Lys—Ser—Thr—Asn—Lys—Phe—Cys—Val—Thr—Cys—

91                                            100
Glu—Asn—Gln—Ala—Pro—Val—His—Phe—Val—Gly—

101       104
Val—Gly—Ser—Cys.
```

* * * * *